US008137365B2

United States Patent
Barker

(10) Patent No.: US 8,137,365 B2
(45) Date of Patent: Mar. 20, 2012

(54) INGUINAL HERNIA REPAIR PROSTHESIS

(75) Inventor: Stephen George Edward Barker, Surrey (GB)

(73) Assignee: Evexar Medical Limited, Bromley, Kent (GB)

( * ) Notice: Subject to any disclaimer, the term of this patent is extended or adjusted under 35 U.S.C. 154(b) by 1008 days.

(21) Appl. No.: 10/542,142

(22) PCT Filed: Jan. 12, 2004

(86) PCT No.: PCT/GB2004/000078
§ 371 (c)(1), (2), (4) Date: Aug. 12, 2005

(87) PCT Pub. No.: WO2004/062530
PCT Pub. Date: Jul. 29, 2004

(65) Prior Publication Data
US 2006/0122637 A1    Jun. 8, 2006

(30) Foreign Application Priority Data
Jan. 14, 2003    (GB) .................................. 0300784.6

(51) Int. Cl.
*A61B 17/08* (2006.01)
*A61F 2/02* (2006.01)

(52) U.S. Cl. ...................... 606/151; 606/213; 623/23.72

(58) Field of Classification Search .................. 606/151, 606/200, 213, 232, 300–321; 623/11.11, 623/13.11–13.2, 14.13, 23.72–23.76, 23.64
See application file for complete search history.

(56) References Cited

U.S. PATENT DOCUMENTS

| 4,769,038 | A | | 9/1988 | Bendavid et al. | |
|---|---|---|---|---|---|
| 5,356,432 | A | * | 10/1994 | Rutkow et al. | 623/23.72 |
| 6,712,859 | B2 | * | 3/2004 | Rousseau et al. | 623/23.64 |
| 2002/0116070 | A1 | * | 8/2002 | Amara et al. | 623/23.74 |

FOREIGN PATENT DOCUMENTS

| EP | 0 614 650 A | 9/1994 |
|---|---|---|
| EP | A-0 614 650 A2 | 9/1994 |
| FR | 2 810 536 A | 12/2001 |
| FR | A-2 810 536 | 12/2001 |
| WO | WO-A-97/45068 | 12/1997 |
| WO | WO 01/97713 A1 | 12/2001 |
| WO | 03/002029 A | 1/2003 |
| WO | WO 03/002029 A1 | 1/2003 |
| WO | 03/011181 A | 2/2003 |
| WO | WO 03/011181 A1 | 2/2003 |
| WO | WO 2004/037123 A1 | 5/2004 |

OTHER PUBLICATIONS

International Search Report of PCT/GB2004/000078, mailed May 12, 2004.

* cited by examiner

*Primary Examiner* — Darwin Erezo
*Assistant Examiner* — Steven Ou
(74) *Attorney, Agent, or Firm* — Nixon & Vanderhye P.C.

(57) ABSTRACT

An implantable prosthesis intended, primarily for the repair of muscle wall defects such as occur in inguinal hernias is fabricated from a surgically compatible mesh material having a prismatic external mesh wall (1). The prismatic shape includes three lobes (2), providing a generally triangular cross-sectional shape. The shape is maintained by internal reinforcing ribs (3), which here extend the length of the prism. The ribs are formed through the connection of three individual mesh strips (4), with each rib comprising two strip parts forming a lamination extending the length of the prism. With this construction closure of elongate legions is readily achieved and a wide range of elongate shapes and dimensions of hernias can be treated.

9 Claims, 2 Drawing Sheets

INGUINAL HERNIA REPAIR PROSTHESIS

Figure 1:
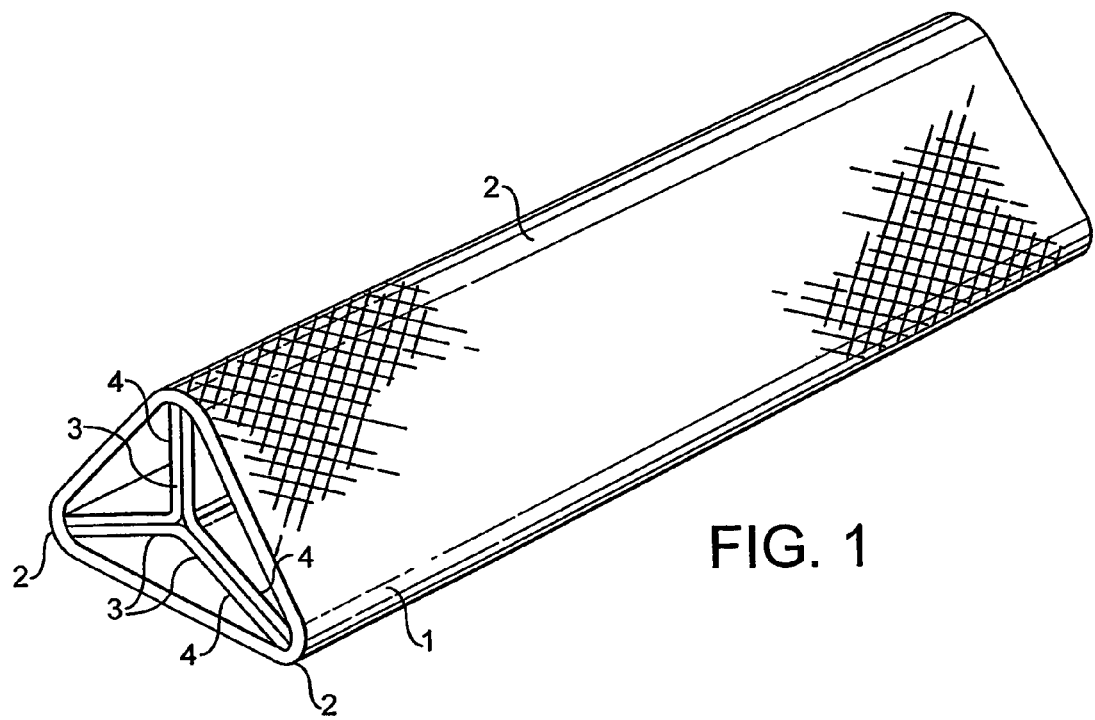

This application is the US national phase of international application PCT/GB2004/000078, filed 12 Jan. 2004, which designated the U.S. and claims priority of GB 0300784.6, filed 14 Jan. 2003, the entire contents of each of which are hereby incorporated by reference.

This invention relates to an implantable prosthesis intended, primarily for the repair of muscle wall defects such as occur in inguinal hernias.

Prosthetic mesh materials are known for the repair and reinforcement of muscle walls. In one technique the mesh is formed into a conical shape forming a plug which is inserted in the hernia defect, often with placement of an additional sheet of flat mesh, to close the defect. In another form, shown in EP 0614650, there is disclosed a conical plug of a mesh material configured with pleats and having inserted petal-like parts. This is stated to have an improved closure performance. The known devices are all useful for, and concerned with, closure of generally localised, or circular plan defects and it has been found that difficulties may occur when the defect opening has a more longitudinal dimension, as is seen with a direct inguinal hernia defect in particular. Here, one or more conical or circular plan plugs is potentially unsatisfactory.

It is one object of this invention to provide an implantable prosthesis which performs to an enhanced degree for inguinal hernias having a more rectangular or elongate opening and in particular, for direct hernias.

According to this invention there is provided an implantable prosthesis for the repair of muscle wall defects such as occur in inguinal hernias, the prosthesis comprising a flexible plug of a surgically compatible mesh material, characterised in that the plug has an elongate form with one portion at least of the surface of the plug forming a projecting longitudinal ridge or bulge.

In a advantageous shape a portion of the surface of the plug may comprise a projecting lobe formed by, or on, the surface. In a preferred arrangement the plug has a prismatic shape with a generally triangular cross-section.

In a preferred prosthesis according to this invention the cross-section of the plug has a three lobed profile. The apices of the lobes may be joined by linear sides, providing a generally triangular cross-section. More than three lobes, or ridges, may be provided.

With a construction of this kind it has been found, surprisingly, that closure of elongate legions is readily achieved and the plug serves for closure of a wide range of elongate shapes and dimensions of hernias.

The elongate mesh material forming the plug preferably has internal longitudinal support webs to support the profile of the mesh. These webs may be an integral part of the mesh configured by folding or formed by separate parts bonded to the inner surface of the outer profile. In another construction three, or more, elongate sub-units may be connected to form the complete prosthesis. Such sub-units may themselves be of a triangular profile.

The wall of the mesh may be pleated circumferentially, or longitudinally to provide a degree of flexibility and compressibility, to facilitate placement into the defect comprising the hernia. For each requirement the mesh plug can be cut to an appropriate required dimension from a stock length piece. This is in contrast to known prostheses which are of predetermined dimensions whose size, for placement, must be judged carefully by the operating surgeon.

In an alternative construction the plug comprises a plurality of individual units connected in a longitudinal side-by-side relationship. Such units may individually have a prismatic profile.

This invention also embraces a construction wherein the plug has an open side being in the form of a triangular profiled trough, the shape then being maintained by internal support formed by mesh material.

Hitherto, a size mis-match issue has proved difficult to resolve with known plugs and the use of two or more plugs is expensive and can lead to unnecessary manipulation during the closure process, Hernia recurrence might occur. The present invention avoids such a basic problem and may be used with elongate and rectangular openings such as found, in particular, with direct inguinal hernia defects to which known plugs may provide an unsatisfactory repair.

The mesh material may be polypropylene and any jointing required may be achieved, for example, by heat sealing. Materials and techniques for the manufacture of surgical mesh materials of the kind useful in carrying out this invention are well known in the art and are not therefore further described in any more detail.

Figure 2:
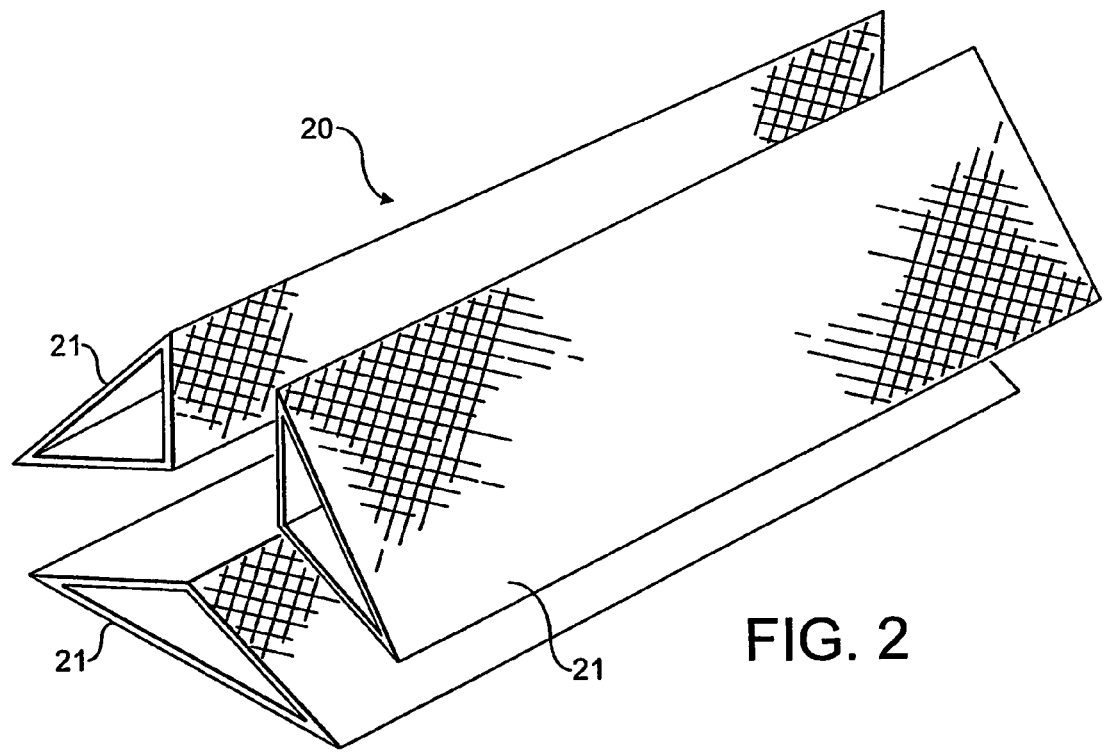
Figure 3:
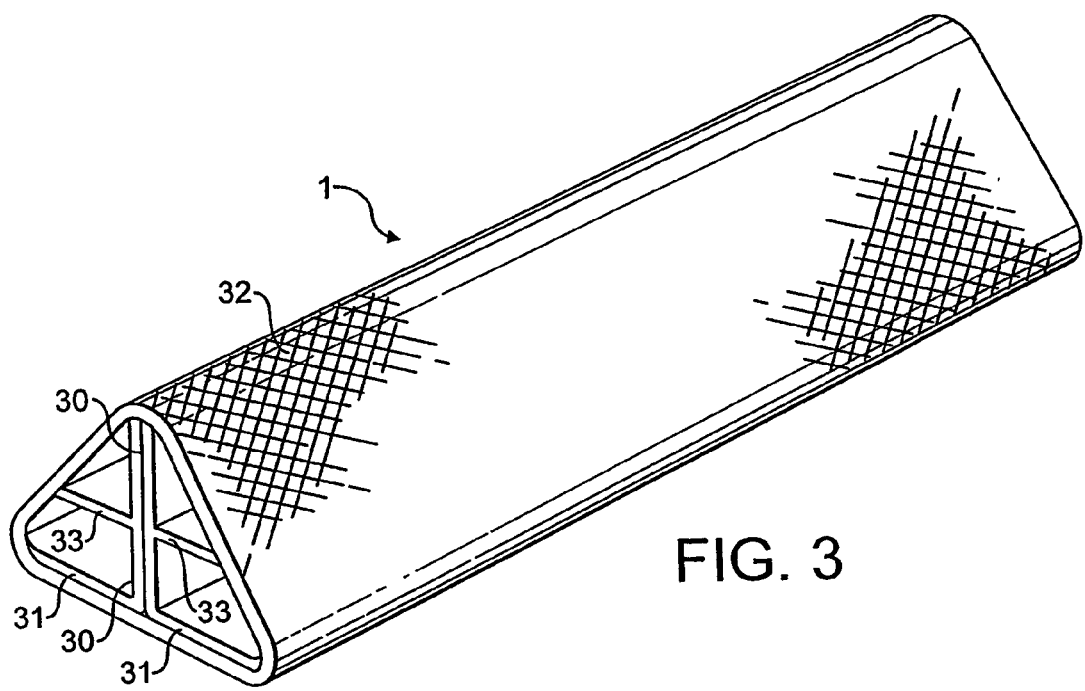
Figure 4:
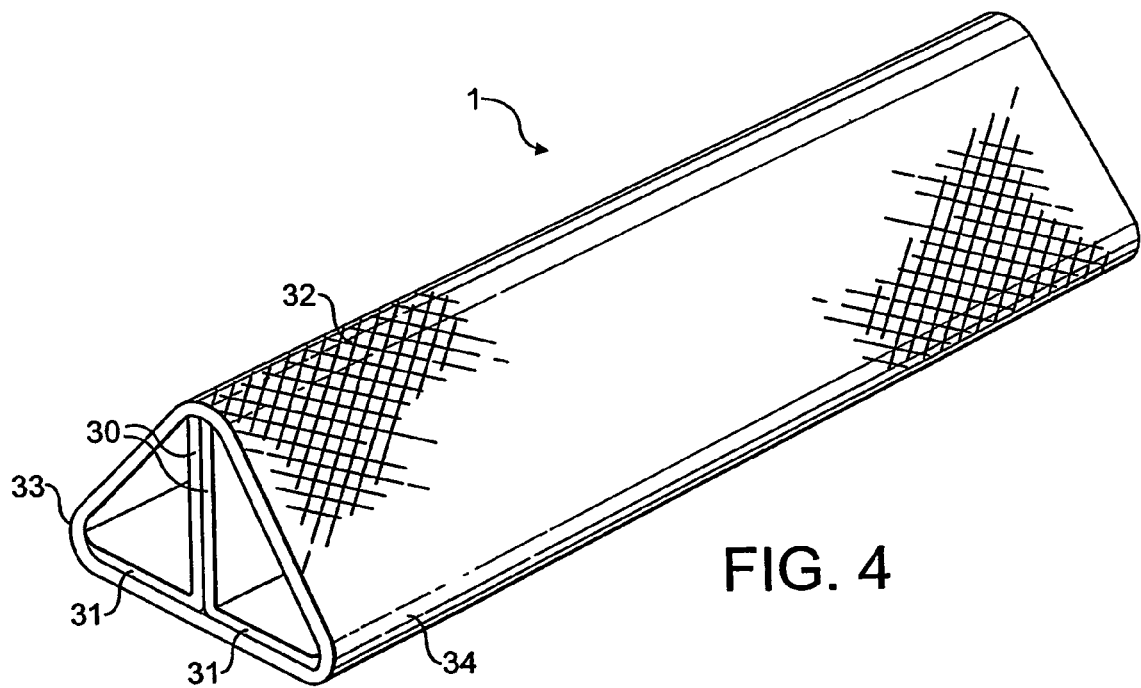

Embodiments according to this invention are described in more detail with reference to examples illustrated in the drawings. In the drawings:

FIG. 1 shows a first embodiment of a prosthesis with internal web support and according to this invention, FIG. 2 shows a second embodiment of prosthesis made from sub-units, FIG. 3 shows a third embodiment of prosthesis with internal support, and FIG. 4 shows a fourth embodiment with a further internal support.

Referring to FIG. 1, an implantable prosthesis intended, primarily for the repair of muscle wall defects such as occur in inguinal hernias is fabricated from a surgically compatible mesh material having a prismatic external mesh wall 1. The prismatic shape includes three lobes 2, providing a generally triangular cross-sectional shape. The shape is maintained by internal reinforcing ribs 3, which here extend the length of the prism, although discrete spaced ribs may be provided for certain applications. The ribs are formed through the connection of three individual mesh strips 4, with each rib comprising two strip parts forming a lamination extending the length of the prism.

FIG. 2 shows a second embodiment according to this invention wherein the prism 20 is formed from three sub-units 21 (shown separated here), with each sub-unit 21 having a triangular shape in cross-section. The sub-units 21 are joined by suitable and known techniques to form the complete prosthesis.

The embodiment shown in FIG. 3, is a variation of that shown in FIG. 1 where the internal supporting ribs comprise two back-to-back L-shaped supports, with the base limbs 31 lying on the lower internal side of the prism and the vertical limbs 30 extending together to the upper lobe 32. Lateral reinforcement 33 may be provided.

FIG. 4 shows a construction similar to FIG. 3 but here the base limbs 31 of the two L-shaped supports 30 extend around the internal profile of the opposed lobes 33 and 34.

In all the embodiments, and according to a feature of this invention, the mesh material may be ridged, pleated, crumpled, or folded to stiffen or pad out the prosthesis this being with particular reference to the internal supports or webs.

In each case, the plug device is intended, primarily for placement into (direct) inguinal hernia defects. From stock lengths, the device can be cut exactly to the correct size. The plug can be sutured into place, or tissues sutured over to hold it in place. The plug may be used with a second, flat, overlying piece of mesh to thus form a tension-free repair.

In contrast to known conical plug devices which, when used together, have gaps between the apices allowing gut penetration, the present invention provides a single elongate plug which can be cut to size thus providing better closure and more resistance to penetration by the gut.

The invention claimed is:

1. An implantable prosthesis for the repair of muscle wall defects, the prosthesis comprising a flexible plug of a surgically compatible mesh material, the plug having an elongate form and comprising an external mesh material wall; wherein:
   the external mesh material wall has three outwardly projecting longitudinal ridges or bulges which provide the plug overall with a closed generally triangular cross-sectional shape; and
   the plug further comprises an internal support extending into contact with respective interiors of at least outermost portions of the outwardly projecting longitudinal ridges or bulges, the internal support extending linearly along the interior of at least a substantial portion of the external mesh material wall between at least two apices of the generally triangular cross-sectional shape and being sufficiently rigid to maintain the size and shape of the external mesh material wall.

2. An implantable prosthesis in accordance with claim 1, wherein the plug has a prismatic shape.

3. An implantable prosthesis in accordance with claim 1, wherein the plug is cut to an appropriate required dimension from a stock length piece.

4. An implantable prosthesis in accordance with claim 3, wherein the mesh material includes at least one joint, said joint being achieved by heat sealing.

5. An implantable prosthesis in accordance with claim 1, wherein the mesh material comprises polypropylene.

6. An implantable prosthesis in accordance with claim 1, wherein the internal support comprises longitudinal webs internally of the external mesh material wall.

7. An implantable prosthesis in accordance with claim 6, wherein the webs are formed by separate parts bonded to an inner surface of the external mesh material wall.

8. An implantable prosthesis in accordance with claim 1, wherein the external mesh material wall comprises means for stiffening the prosthesis.

9. An implantable prosthesis for the repair of muscle wall defects, the prosthesis comprising a flexible plug of a surgically compatible mesh material, the plug having an elongate form and comprising an external mesh material wall; wherein:
   the external mesh material wall has three outwardly projecting longitudinal ridges or bulges which provide the plug overall with a closed generally triangular cross-sectional shape; and
   the plug further comprises an internal support extending into contact with respective interiors of at least outermost portions of the outwardly projecting longitudinal ridges or bulges, the internal support being sufficiently rigid to maintain the size and shape of the external mesh material wall, wherein the internal support comprises a pair of L-shaped supports positioned back to back and extending into the outwardly projecting longitudinal ridges or bulges.

* * * * *